(12) United States Patent
Kim et al.

(10) Patent No.: US 9,358,075 B2
(45) Date of Patent: Jun. 7, 2016

(54) SURGICAL ROBOT SYSTEM AND METHOD OF OPERATING THE SAME

(71) Applicant: SAMSUNG ELECTRONICS CO., LTD., Suwon-si, Gyeongg-do (KR)

(72) Inventors: Hyung-joo Kim, Seongnam-si (KR); Yo-an Lim, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 312 days.

(21) Appl. No.: 13/959,063

(22) Filed: Aug. 5, 2013

(65) Prior Publication Data

US 2014/0257328 A1   Sep. 11, 2014

(30) Foreign Application Priority Data

Mar. 8, 2013   (KR) .......................... 10-2013-0025254

(51) Int. Cl.
*A61B 19/00*   (2006.01)

(52) U.S. Cl.
CPC ......... *A61B 19/2203* (2013.01); *A61B 19/5212* (2013.01); *A61B 2019/2223* (2013.01); *Y10S 901/47* (2013.01)

(58) Field of Classification Search
CPC ............... A61B 19/22; A61B 19/2203; A61B 19/2211; A61B 19/2215; A61B 19/2223; A61B 19/223; A61B 19/2234; A61B 19/2242; A61B 19/2269; A61B 19/2276; A61B 19/5212; A61B 2019/2223; Y10S 901/47
See application file for complete search history.

(56) References Cited

U.S. PATENT DOCUMENTS

| | | | |
|---|---|---|---|
| 5,454,827 A * | 10/1995 | Aust et al. ..................... 606/170 |
| 8,749,190 B2 * | 6/2014 | Nowlin et al. ........... 318/568.21 |
| 2006/0167440 A1 * | 7/2006 | Cooper et al. ..................... 606/1 |
| 2010/0082041 A1 * | 4/2010 | Prisco ............................ 606/130 |
| 2011/0071508 A1 * | 3/2011 | Duval et al. ........................ 606/1 |
| 2011/0098719 A1 * | 4/2011 | Llinas et al. .................. 606/129 |
| 2011/0264109 A1 | 10/2011 | Nowlin et al. |
| 2013/0178867 A1 * | 7/2013 | Farritor et al. ................ 606/130 |

FOREIGN PATENT DOCUMENTS

| | | |
|---|---|---|
| JP | 2009-160011 | 7/2009 |
| JP | 2012-20156 | 2/2012 |
| KR | 10-2011-0030034 | 3/2011 |
| KR | 10-1181569 | 9/2012 |

* cited by examiner

*Primary Examiner* — Jerrah Edwards
*Assistant Examiner* — Tamara Weber
(74) *Attorney, Agent, or Firm* — Harness, Dickey & Pierce, P.L.C.

(57) ABSTRACT

A surgical robot system for a single port surgery includes: a first robot arm in which a joint-type instrument is installed and providing a motion displacement to the joint-type instrument with respect to a remote center of motion (RCM); and a second robot arm pairing the first robot arm, in which a non-joint-type instrument is installed and providing a motion displacement to the non-joint-type instrument with respect to the RCM.

16 Claims, 10 Drawing Sheets

SURGICAL ROBOT SYSTEM AND METHOD OF OPERATING THE SAME

CROSS-REFERENCE TO RELATED APPLICATIONS

This application claims the benefit of Korean Patent Application No. 10-2013-0025254, filed on 8 Mar. 2013, in the Korean Intellectual Property Office, the disclosure of which is incorporated herein in its entirety by reference.

BACKGROUND

1. Field

One or more embodiments relate to a surgical robot system comprising a plurality of robot arms in which a surgical instrument is installed and a method of operating the surgical robot system.

2. Description of the Related Art

As minimally invasive surgery using a surgical robot has received a great deal of attention in recent years, much research has been performed in this area and associated developments have largely occurred. A surgical robot system performs a surgical operation by inserting a surgical instrument installed in a robot arm into the abdominal cavity or a joint region of a patient.

For a smooth and efficient surgical operation, the surgical instrument is required to have a high operating force, a large workspace, and a dexterous motion with a high degree of freedom. However, it is difficult to embody such a surgical robot system satisfying the above requirements. In particular, satisfying these requirements is quite difficult for a single port surgical robot system for performing a surgical operation through a single path (opening).

SUMMARY

The foregoing described problems may be overcome and/or other aspects may be achieved by one or more embodiments of surgical robot systems having a dexterous motion with a high operating force and a high degree of freedom.

Additional aspects and/or advantages of one or more embodiments will be set forth in part in the description which follows and, in part, will be apparent from the description, or may be learned by practice of one or more embodiments of disclosure. One or more embodiments are inclusive of such additional aspects.

One or more embodiments relate to a surgical robot system for a single port surgery that may include a first robot arm in which a joint-type instrument may be installed and that may provide a motion displacement to the joint-type instrument with respect to a remote center of motion (RCM); and a second robot arm that may be paired with the first robot arm, in which a non-joint-type instrument may be installed and that may provide a motion displacement to the non-joint-type instrument with respect to the RCM.

The surgical robot system may further include: a third robot arm in which an endoscopic camera may be installed and that may provide a motion displacement to the endoscopic camera with respect to the RCM, wherein the third robot arm may be disposed in the opposite direction of the first robot arm with respect to the second robot arm.

The first robot arm and the second robot may form a first arm module, wherein the surgical robot system may further including a second arm module that may have a symmetrical structure with the first arm module.

Second robot arms of the first arm module and the second arm module may be disposed to be adjacent to each other.

The surgical robot system may further include: a third robot arm in which an endoscopic camera may be installed and that may provide an RCM displacement to the endoscopic camera, wherein the third robot arm may be disposed between the first arm module and the second arm module.

The non-joint-type instrument may be a linear-type instrument.

One or more embodiments relate to a surgical robot system for a single port surgery that may include a first robot arm in which a joint-type instrument including an elbow joint portion may be installed; and a second robot arm that may pair with the first robot arm and in which a non-joint-type instrument may be installed.

The joint-type instrument and the non-joint-type instrument may be inserted into a patient to form a triangular structure.

The first robot arm and the second robot may form a first arm module, wherein the surgical robot system may further include a second arm module that may have a symmetrical structure with the first arm module.

Second robot arms of the first arm module and the second arm module may be disposed to be adjacent to each other.

The first robot arm and the second robot arm may provide a motion displacement with respect to an RCM to the joint-type instrument and the non-joint-type instrument, respectively.

The elbow joint portion may include a shaft pivotally connect to at least one of a first portion and a second portion of the first robot arm; an actuation rod connected to the first portion of the first robot arm; a joint link connected to the actuation rod and to the second portion of the first robot arm. When the actuation rod is pulled in a longitudinal direction with respect to the first portion of the first robot arm, the pulling force may be transferred to the second portion of the first robot arm via the joint link.

The joint link may be formed of an elastic material.

The joint link is formed of a rigid material.

One or more embodiments relate to a method of operating a surgical robot system for a single port surgery, wherein the method may include preparing a first robot arm providing a motion displacement to a joint-type instrument with respect to a remote center of motion (RCM) and a second robot arm providing a motion displacement to a non-joint-type instrument with respect to the RCM; inserting the joint-type instrument and the non-joint-type instrument into a patient through a single port; and bending an elbow joint portion of the joint-type instrument and forming a triangular structure using the joint-type instrument and the non-joint-type instrument.

The method may further include: linearly moving the non-joint-type instrument in a lengthwise direction.

The method may further include: pivoting the joint-type instrument with respect to the RCM and actuating the elbow joint portion.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Figure 1:
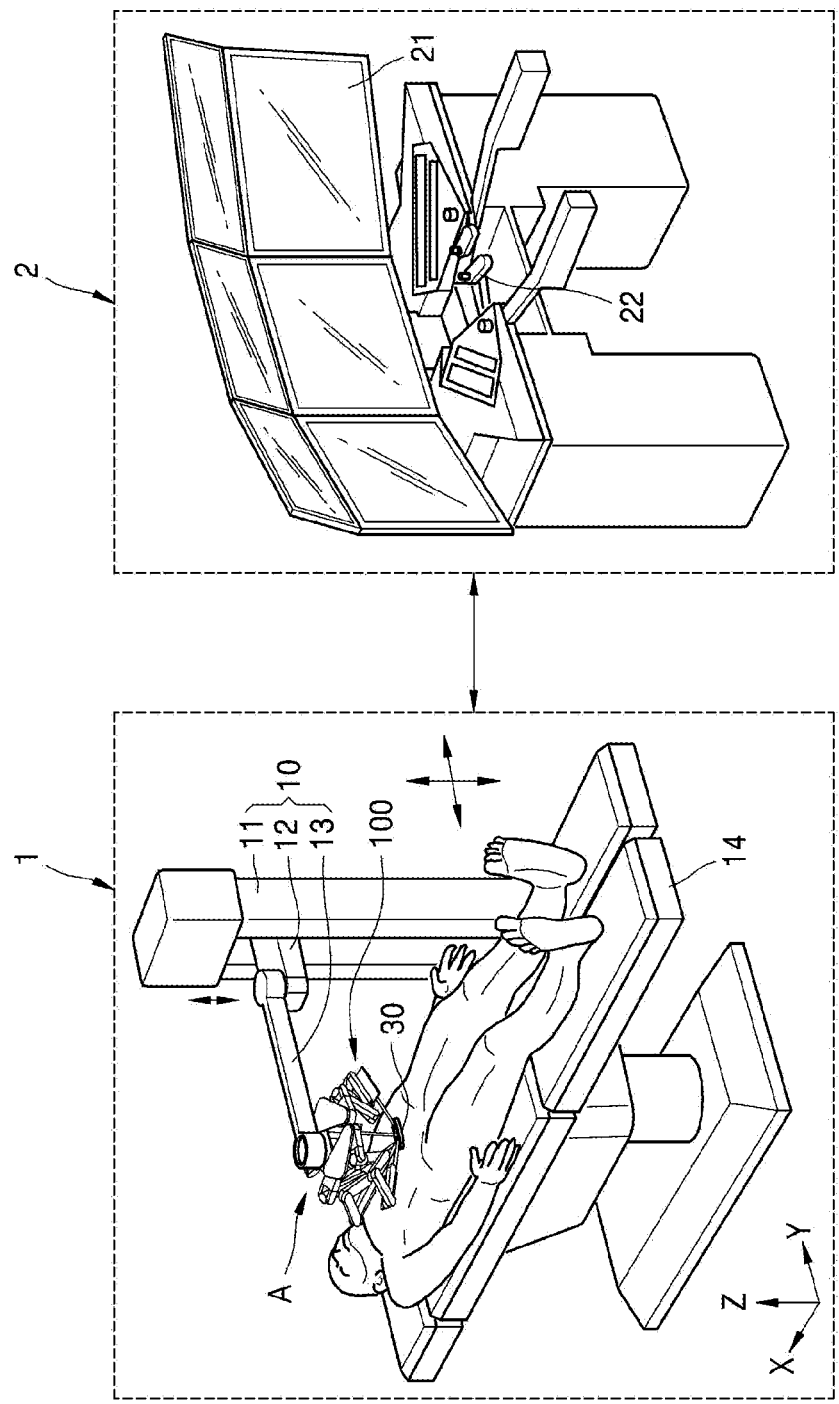
FIG. 1 is a perspective view illustrating the structure of a surgical robot system according to one or more embodiments.

Reference will now be made in detail to one or more embodiments, illustrated in the accompanying drawings, wherein like reference numerals refer to like elements throughout. In this regard, embodiments of the present invention may be embodied in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the present invention.

[Surgical Robot System]

Figure 2:
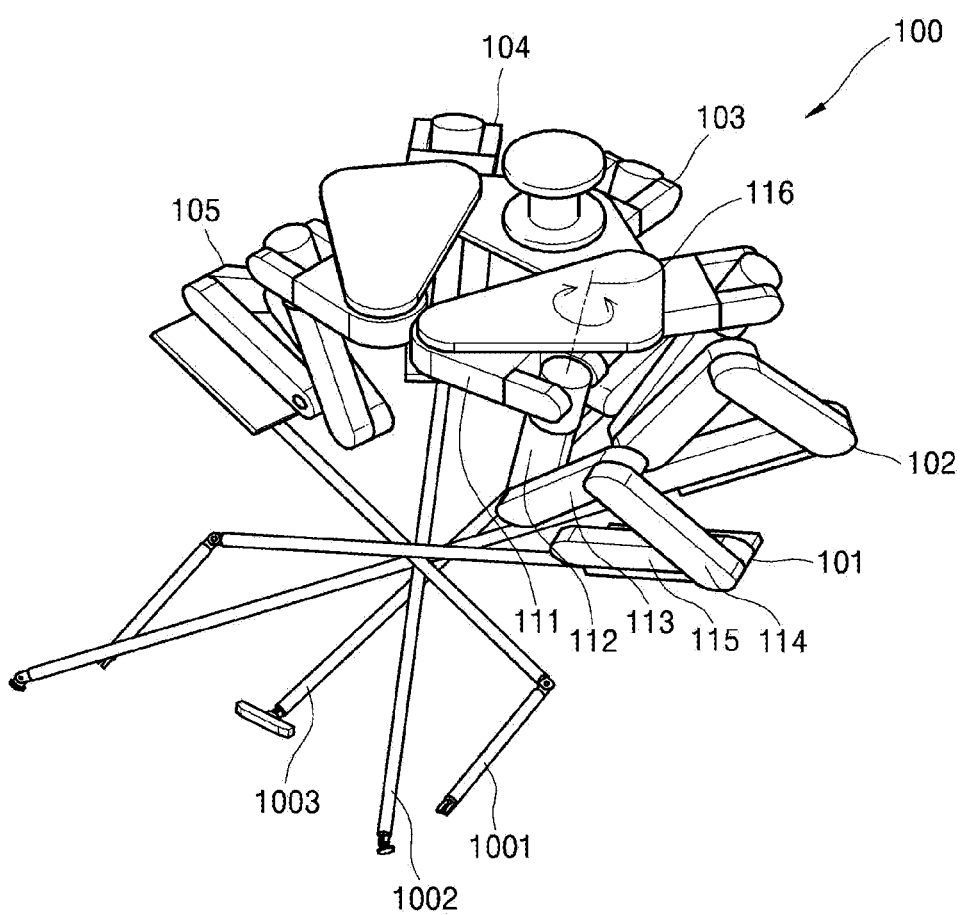
FIG. 2 is a detailed perspective view illustrating a portion A of FIG. 1.

FIG. 1 is a perspective view illustrating the structure of a surgical robot system according to one or more embodiments. FIG. 2 is a detailed perspective view illustrating a portion A of FIG. 1. Referring to FIGS. 1 and 2, the surgical robot system may be used to perform a surgical operation on a patient by inserting surgical instruments 1001 and 1002 and an endoscopic camera 1003 into the patient through an incision portion 30, observing the inside of the patient through an image captured by the endoscopic camera 1003, and controlling the surgical instruments 1001 and 1002. The surgical robot system may include a surgical station 1 equipped with mechanical apparatuses for performing a surgical operation on the patient and a control station 2 for controlling the surgical station 1.

The surgical station 1 may include a robot arm unit 100 that may include a plurality of robot arms 101~105 in which the surgical instruments 1001 and 1002 may be installed and a positioning unit 10 for positioning the robot arm unit 100 at a desired position, for example, a position corresponding to the incision portion 30 provided in the patient.

For example, the positioning unit 10 may include a vertical column 11 having an elevation block 12 elevating in a vertical direction, that is, in a z-axis direction, and a positioning arm 13 having an end portion where the robot arm unit 100 may be provided. The vertical column 11 may be moved in a horizontal direction, for example, in an x-axis direction and/or a y-axis direction. For example, the vertical column 11 may be supported to be able to move in the x-axis direction and/or a y-axis direction with respect to an operation table 14 where a patient lies. Furthermore, the positioning arm 13 may be coupled to the elevation block 12 to be capable of pivoting around, for example, the z-axis.

The control station 2 may include an image display unit 21 for displaying an image that may be transferred through an image capturing device, for example, the endoscopic camera 1003, inserted into the patient, and a manipulation unit 22. The manipulation unit 22 may control movements of the positioning unit 10, the robot arm unit 100, and the surgical instruments 1001 and 1002, and may include, for example, one or more haptic manipulating devices, such as a joystick. The robot arms 101~105 and the surgical instruments 1001 and 1002 may be connected to the control station 2 in wired form and/or wirelessly. A surgeon may perform a surgical operation by manipulating the manipulation unit 22 to actuate the robot arms 101~105 and the surgical instruments 1001 and 1002.

[Robot Arm Units]

Referring to FIG. 2, the robot arm unit 100 may include robot arms 101~105. The surgical robot system of the present embodiment may be used to perform a single port surgery. The surgical instruments 1001 and 1002 installed in the robot arms 101~105 may be inserted into the patient through the single incision portion 30. The robot arms 101~105 may allow the surgical instruments 1001 and 1002 to move around a remote center of motion (RCM) near the incision portion 30. The robot arms 101~105 may have a multi-joint structure that may provide the surgical instruments 1001 and 1002 with the RCM. According to one or more embodiments, each of the robot arms 101~105 may include five arms 111~115 that may be pivotally connected to one another in series, as shown in FIG. 2. For example, the arm 112 may be pivotally connected to the arm 111 with respect to a pivot axis 116. The surgical instruments 1001 and 1002 may be installed in the arms 115 of the robot arms 101~105. However, the multi-joint structure of the robot arms 101~105 is not limited to the example of FIG. 2.

The surgical instruments 1001 and 1002 may be respectively a joint-type instrument and a non-joint-type instrument (hereinafter, the surgical instruments 1001 and 1002 are respectively referred to as the joint-type instrument and the non-joint-type instrument). The joint-type instrument 1001 may be an instrument that may include an elbow joint portion (1600 of FIG. 3) having a bending motion. The non-joint-type instrument 1002 may be an instrument that may not include the elbow joint portion (1600 of FIG. 3). That is, the non-joint-type instrument 1002 may be a linear-type instrument. Examples of the joint-type instrument 1001 and the non-joint-type instrument 1002 will now be described below.

[Joint-Type Instrument]

Figure 3:
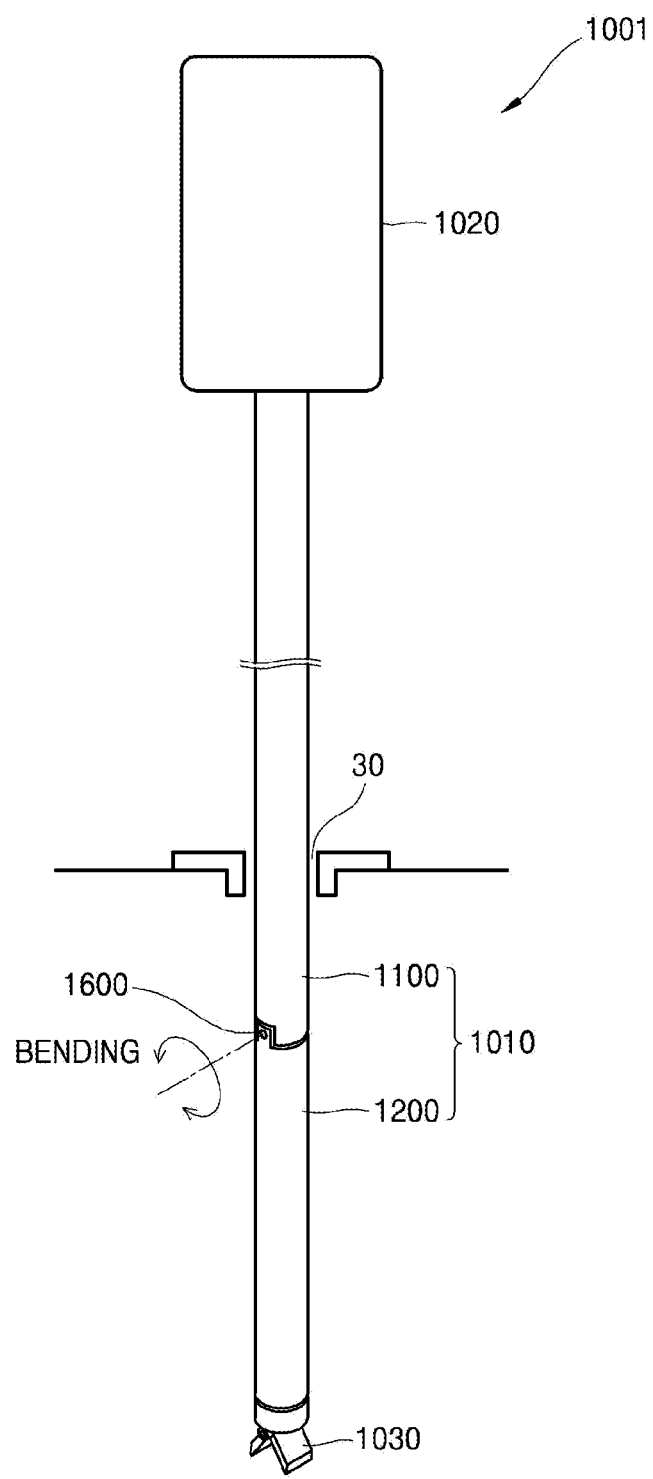
FIG. 3 illustrates a joint-type instrument according to one or more embodiments.

FIG. 3 illustrates the joint-type instrument 1001 according to one or more embodiments. Referring to FIG. 3, the joint-type instrument 1001 may include an extension portion 1010 and a head portion 1020. The extension portion 1010 may have a shape of a long rod and may be inserted into, for example, the abdominal cavity or a joint region of a patient to approach an affected part. The extension portion 1010 may have a shape of a hollow pipe through which an actuation tool for actuating the elbow joint portion 1600, a surgical tool 1030, and a wrist joint portion (not shown) that will be described later, may pass. The surgical tool 1030 for performing a detailed surgical operation, such as an incision or suture, via manipulation of a surgeon may be provided at an end portion of the extension portion 1010. The surgical tool 1030 may be, for example, a surgical knife, surgical forceps, surgical scissors, cautery (a tool for burning or cutting an affected part by using electric energy or thermal energy), an endoscopic camera, etc.

The extension portion 1010 may be provided with the elbow joint portion 1600. The elbow joint portion 1600 bends within a patient via manipulation of the surgeon, and thus providing an additional degree of freedom besides an RCM provided by the robot arms 101~105. The elbow joint portion 1600 may be a joint portion capable of bending actuation.

For bending actuation, an actuation structure using a wire and a slider-crank actuation structure using a rigid rod may be adopted. The actuation structure to slide the rigid rod is advantageous in transferring a large force, compared to the actuation structure using a wire. An example of the slider-crank actuation structure using the rigid rod will now be described.

Figure 4:
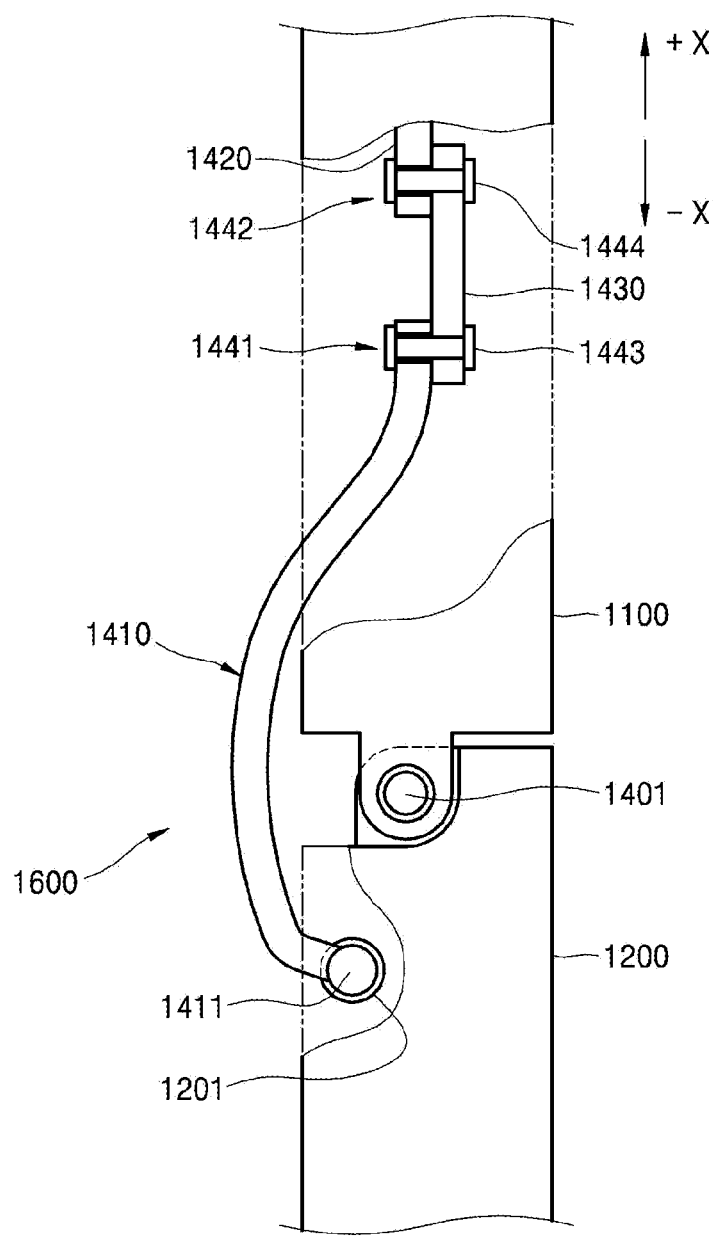
FIG. 4 illustrates an example of a joint structure of an elbow joint portion according to one or more embodiments.
Figure 5:
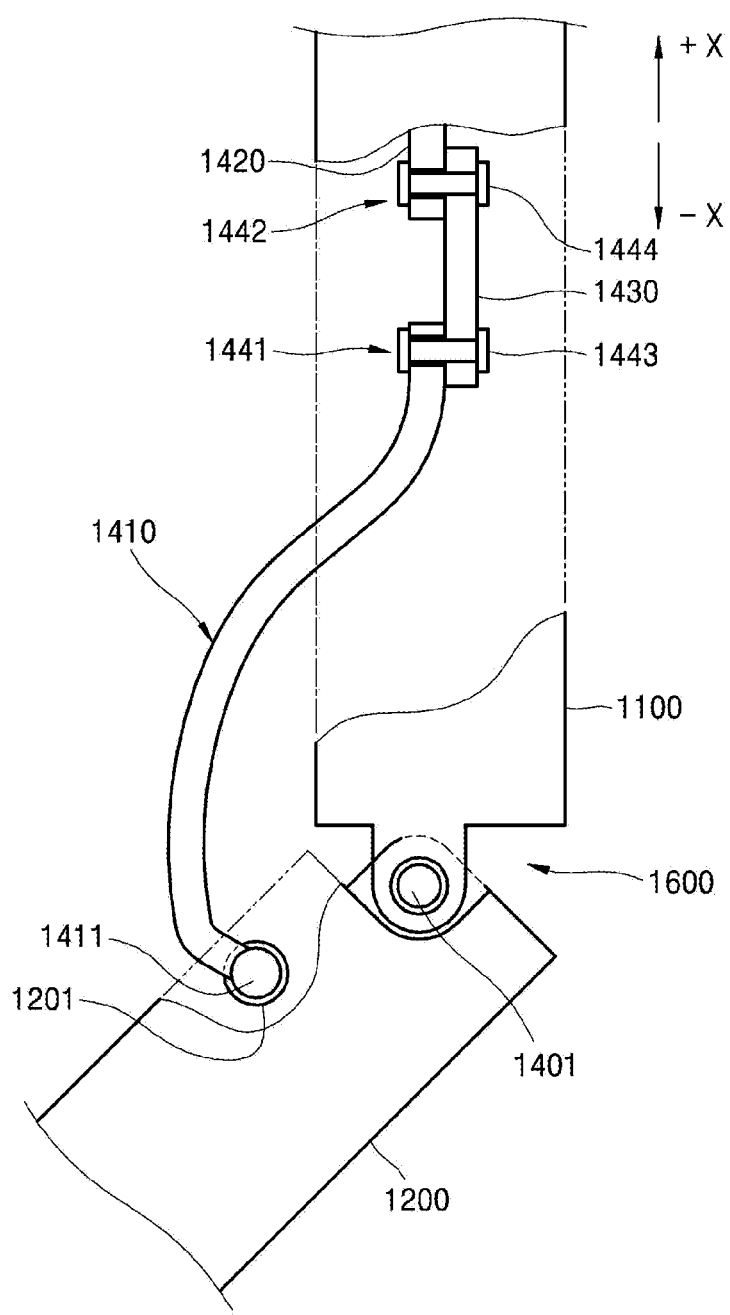
FIG. 5 illustrates a state of a second arm according to one or more embodiments in a pivoting state, such as the joint structure of an elbow joint portion of FIG. 4.

FIGS. 4 and 5 illustrate the elbow joint portion 1600 for bending actuation, according to one or more embodiments. Referring to FIGS. 4 and 5, the extension portion 1010 may include a first arm 1100 and a second arm 1200. The first arm 1100 may extend from the head portion 1020. The second arm 1200 may be pivotally connected to an end portion of the first arm 1100. The surgical tool 1030 may be installed in an end portion of the second arm 1200. Although not shown, a wrist joint portion (not shown) for providing an additional degree of freedom to the surgical tool 1030 may be further disposed between the surgical tool 1030 and the end portion of the second arm 1200. The wrist joint portion may be, for example, a joint portion capable of yawing and/or pitching. However, whether the wrist joint portion exists or not is a basis for identifying the joint-type instrument 1001 and the non-joint-type instrument 1002.

For example, a shaft 1401 may be fixed to the first arm 1100, and the second arm 1200 may be pivotally connected to the shaft 1401. Alternatively, the shaft 1401 may be fixed to the second arm 1200, and the first arm 1100 may be pivotally connected to the shaft 1401. Alternatively, the first and second arms 1100 and 1200 may be pivotally connected to the shaft 1401 with a clearance fit. In this case, a stop member (not shown), for example, an E-ring, for preventing the shaft 1401 from deviating in a lengthwise direction thereof, may be coupled to the shaft 1401.

An actuation rod 1420 may be provided at the first arm 1100. The actuation rod 1420 may be disposed in the first arm 1100 and reciprocally actuated in a lengthwise direction of the first arm 1100. A structure of reciprocally actuating the actuation rod 1420 in the lengthwise direction is described below with reference to FIG. 6. A joint link 1410 may be actuated by the actuation rod 1420 to allow the second arm 1200 to pivot around the shaft 1401. One end portion of the joint link 1410 may be connected to the second arm 1200, and the other end portion thereof may be connected to the actuation rod 1420. The joint link 1410 may be connected to the second arm 1200 by, for example, a pin 1411, to be capable of pivoting, for example, in the same direction as a pivot direction of the second arm 1200. For example, the pin 1411 may be fixed to the second arm 1200, and the one end portion of the joint link 1410 may be pivotally connected to the pin 1411 in a clearance fit. Alternatively, the pin 1411 may be fixed to the joint link 1410 or integrally formed with the join link 1410, and the pin 1411 may be inserted into a through-hole portion 1201 provided in the second arm 1200. Although it is not illustrated in the drawings, the other end portion of the joint link 1410 may be directly connected to the actuation rod 1420. In this case, the other end portion of the joint link 1410 may be pivotally connected to the actuation rod 1420. The pivotal axis of the joint link 1410 may be, for example, parallel with or perpendicular to the pivotal axis of the second arm 1200. Also, as illustrated in FIG. 4, the other end portion of the joint link 1410 may be connected to the actuation rod 1420 via an intermediate member 1430. At least one of a first connection portion 1441 between the other end portion of the joint link 1410 and the intermediate member 1430 and a second connection portion 1442 between the intermediate member 1430 and the actuation rod 1420 may have a connection structure that may be capable of pivoting in at least one direction. The pivotal axis of any of the first connection portion 1441 and the second connection portion 1442 may be, for example, parallel with or perpendicular to the pivotal axis of the second arm 1200. In one or more embodiments, each of the first and second connection portions 1441 and 1442 may have a connection structure that is capable of pivoting. The first connection portion 1441 that is capable of pivoting may have, for example, a structure in which a pin 1443 provided at the intermediate member 1430 is inserted in a through hole (not shown) provided in the other end portion of the joint link 1410 and having a diameter greater than that of the pin 1443. The second connection portion 1442 that is capable of pivoting may have, for example, a structure in which a pin 1444 provided at the intermediate member 1430 is inserted in a through hole (not shown) provided in the actuation rod 1420 and having a diameter greater than that of the pin 1444.

The joint link 1410 may be an elastic body formed of an elastic material. The elastic material may be a superelastic material. For example, the joint link 1410 may be formed of an elastic material, such as a shape memory alloy (SMA). The SMA may be, for example, Ni—Ti, Cu—Zn, Cu—Zn—Al, Cu—Al—Ni, etc. The shape of the joint link 1410 is not particularly restricted. The cross-sectional shape of the joint link 1410 may be constant and, in some cases, may not be constant such that a large amount of deformation may occur in a particular portion. The joint link 1410 may be a non-elastic body. In this case, the intermediate member 1430 may be formed of an elastic material, such as a leaf spring.

The distance between the pin 1411 and the shaft 1401 may be greater than the diameters of the first and second arms 1100 and 1200. For example, the distance between the pin 1411 and the shaft 1401 may be about 1.5 times or more, particularly, about 1.5 to 3 times, greater than the diameters of the first and second arms 1100 and 1200. When a force to reciprocate the actuation rod 1420 is determined, a stronger moment may be generated as the distance between the pin 1411 and the shaft 1401 increases. Also, the actuation rod 1420 may be a rigid body and may be, for example, a steel rod having a diameter of, for example, about 2 mm. The joint structure using the actuation rod 1420 that is a rigid body may transfer a stronger force to a joint, compared to a structure using a wire. Thus, by using the surgical instrument 1001, a surgical operation may be performed with a strong force.

According to the above-described structure, when the actuation rod 1420 is pulled by an actuator (not shown) in a +X direction of FIG. 4, the pulling force may be transferred to the second arm 1200 via the joint link 1410, and thus, the second arm 1200 may pivot around the shaft 1401 as illustrated in FIG. 5. Accordingly, the joint link 1410 that is an elastic body may be elastically deformed to a certain degree and may absorb a bending stress applied to a connection portion between the joint link 1410 and the actuation rod 1420 according to a location change in the shaft 1401. When the joint link 1410 is a non-elastic body, the intermediate member 1430 that is an elastic body may be elastically deformed, and thus, a bending stress may be absorbed. In the state of FIG. 5, when the actuation rod 1420 is pushed in a −X direction, the second arm 1200 pivots to reach the state as shown in FIG. 4.

Figure 6:
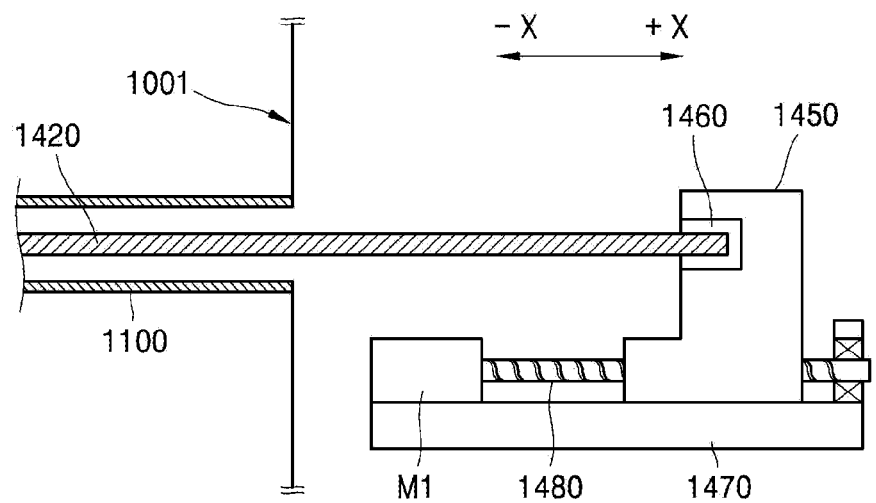
FIG. 6 illustrates an example of an actuation structure to actuate an elbow joint structure according to one or more embodiments, such as the elbow joint portion of FIG. 4.

FIG. 6 illustrates an example of a rod actuation portion provide in the head portion 1020 to actuate the actuation rod 1420 to reciprocate in a lengthwise direction. Referring to FIG. 6, according to the surgical instrument 1001 of one or more embodiments, one end portion of the actuation rod 1420 may be fixed to a mobile block 1450 by a clamp 1460. The mobile block 1450 may be supported on a base 1470 to be capable of moving in a lengthwise direction of the actuation rod 1420. To move the mobile block 1450, a lead screw 1480 rotated by, for example, a motor M1, may be employed. The lead screw 1480 may penetrate the mobile block 1450 and may be supported on the base 1470. A screw thread to be engaged with a screw portion of the lead screw 1480 may be provided on the mobile block 1450.

In the above-described structure, the mobile block 1450 may be moved back and forth by rotating the motor M1, and thus, the actuation rod 1420 may be reciprocated in the −X and +X directions.

Figure 7:
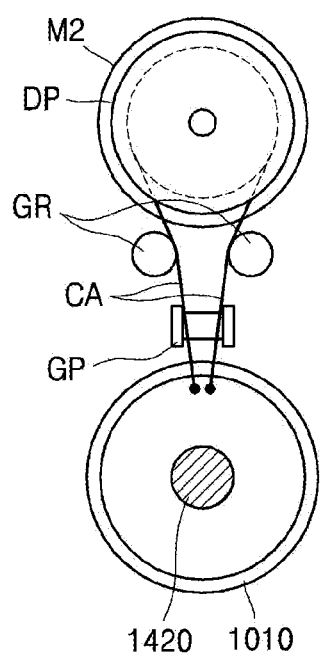
FIG. 7 illustrates an example of a structure to actuate a surgical tool using a wire according to one or more embodiments.

An actuator for actuating the surgical tool 1030 may be provided in the head portion 1020. Referring to FIG. 7, a wire CA for actuating the surgical tool 1030 is illustrated. The wire CA may pass through the inside of the extension portion 1010 having a shape of a hollow pipe to be connected to the surgical tool 1030. A motor M2 for actuating the wire CA may be provided in the head portion 1020. The wire CA may be guided by a guide pulley GP and a guide roller GR and may be wound around a driving pulley DP that is rotated by the motor M2. In the above structure, the surgical tool 1030 may be actuated by rotating the motor M2 forwardly and backwardly and pulling the wire CA in a desired direction.

If the surgical instrument 1001 is installed in the robot arms 101~105, the motors M1 and M2 may be connected to the control station 2 via wires or wirelessly. Although not shown, for example, a first gear (not shown) connected to the lead screw 1480 may be installed instead of the motor M1 for actuating the lead screw 1480, and a second gear (not shown) connected to the driving pulley DP may be installed instead of the motor M2 for actuating the wire CA. In this case, first and second actuation motors (not shown) for actuating the first and second gears may be provided in the robot arms 101~105. If the surgical instrument 1001 is installed in the robot arms 101~105, the first and second gears may be respectively connected to the first and second actuation motors, thereby actuating the elbow joint portion 1600 and the surgical tool 1030.

The actuator of FIG. 7 is merely an example, and an actuator employing two or more wires may be provided in the head portion 1020 according to a type of the surgical tool 1030. When a wrist joint portion (not illustrated) is provided, an actuator for actuating the wrist joint portion may be further provided in the head portion 1020.

[Non-Joint-Type Instrument]

Figure 8:
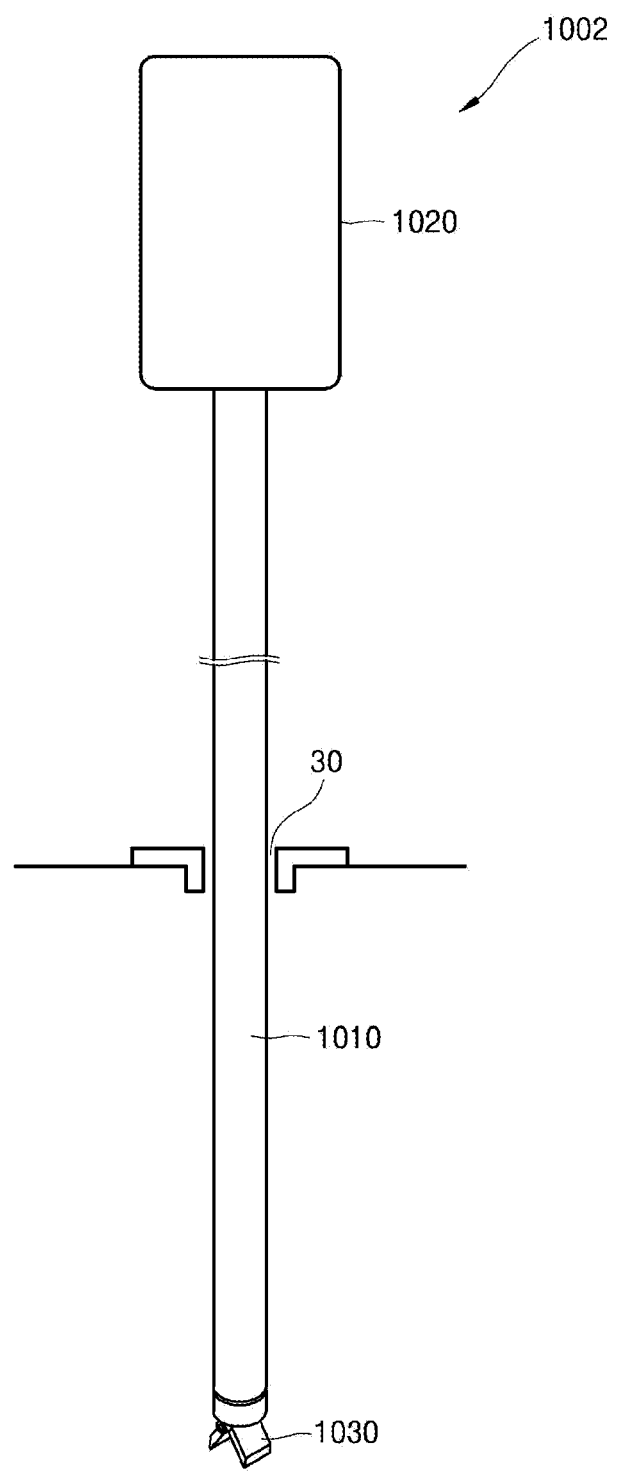
FIG. 8 illustrates a non-joint-type instrument according to one or more embodiments.

FIG. 8 illustrates the non-joint-type instrument 1002 according to one or more embodiments. The non-joint-type instrument 1002 may have the same structure as the joint-type instrument 1001 and the head portion 1020 of FIGS. 3 and 7, except that the non-joint-type instrument 1002 does not include the elbow joint portion 1600. The non-joint-type instrument 1002 may be a linear-type instrument.

Although not shown, a wrist joint portion (not shown) for providing an additional degree of freedom to the surgical tool 1030 may be further disposed between the surgical tool 1030 and an end portion of the extension portion 1010. The wrist joint portion may be, for example, a joint portion capable of yawing and/or pitching. However, whether the wrist joint portion exists or not is a basis for identifying the joint-type instrument 1001 and the non-joint-type instrument 1002.

[Structure for Single Path Surgery]

Figure 9A:
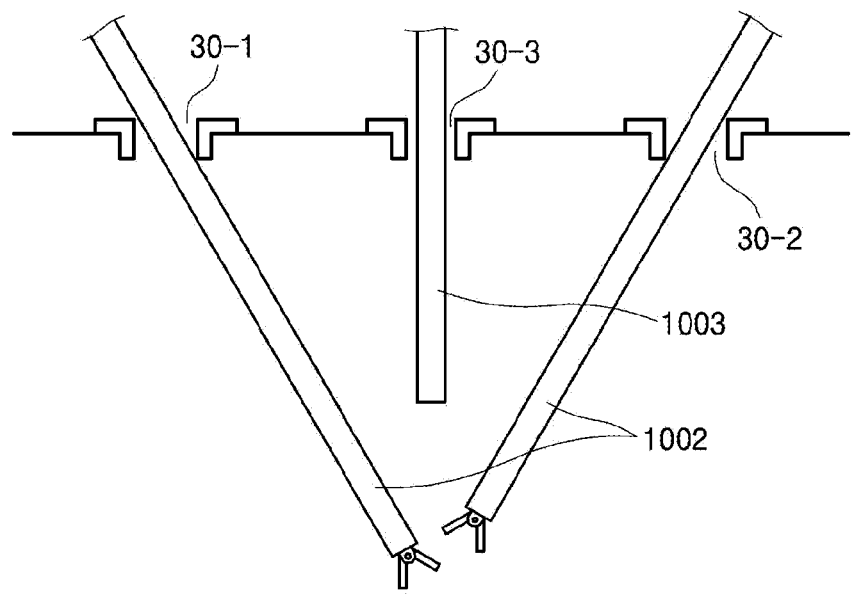
FIG. 9A is a conceptual view of a multi-port surgery according to one or more embodiments.
Figure 9B:
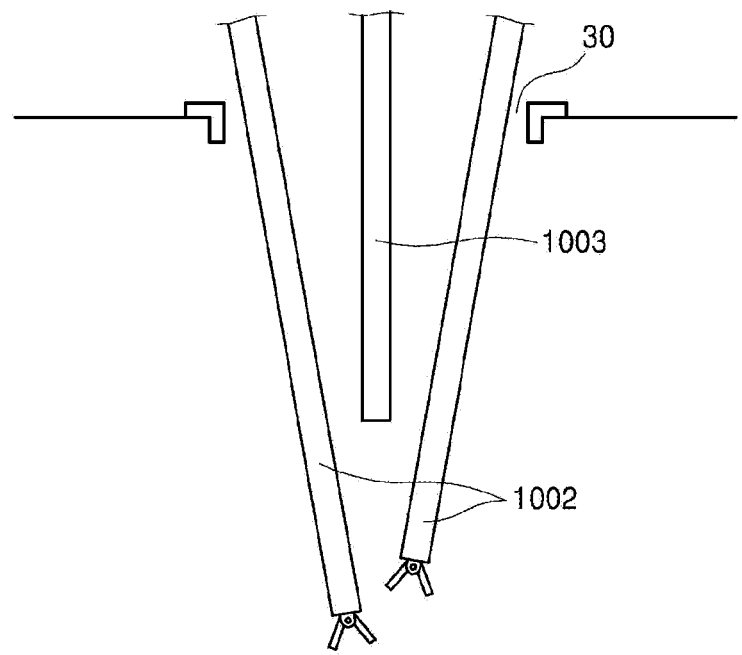
FIG. 9B illustrates two non-joint-type instruments that form a triangular structure in a single port surgery according to one or more embodiments.
Figure 9C:
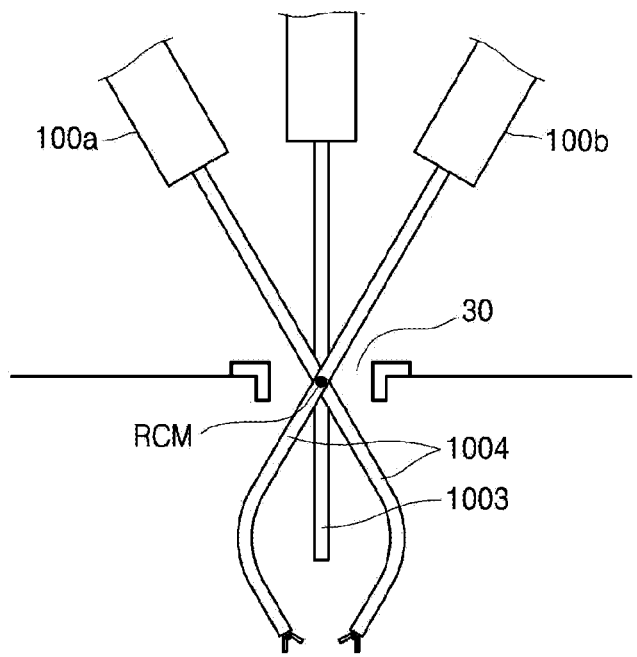
FIG. 9C illustrates two bent instruments that form a triangular structure in a single port surgery according to one or more embodiments.

For a robot surgery, a pair of instruments may be disposed in a triangular structure having an affected part as an apex after being inserted into the patient through the incision portion 30. For example, as shown in FIG. 9A, in a multi-port surgery using three incision portions 30-1, 30-2, and 30-3, the non-joint-type instrument 1002 may be inserted into the incision portions 30-1 and 30-2 to form the triangular structure. The endoscopic camera 1003 may be inserted through the incision portion 30-3. However, in a single port surgery, as shown in FIG. 9B, it is difficult to form the triangular structure by using the two non-joint-type instruments 1002, and a size of the incision portion 30 needs to be increased to secure a work space. As shown in FIG. 9C, two bent instruments 1004 may be obliquely disposed to form the triangular structure having the affect part as the apex. However, in this case, a space for moving robot arms 100a and 100b that actuate the instruments 1004 is small such that the instruments 1004 may be actuated so as to avoid interference between robot arms 100a and 100b. For example, the farther the affected part is disposed away from the incision portion 30, the closer the robot arms 100a and 100b are. That is, the robot arms 100a and 100b move in a direction of an arrow E of FIG. 9D and concurrently move together around the RCM in a direction F so as to form the triangular structure having the affected part as an apex. Thus, interference between the robot arms 100a and 100b may occur, which makes it difficult to secure a large workspace and limits actuation freedom of the instruments 1004. When the endoscopic camera 1003 is inserted, an actuation range of the robot arms 100a and 100b is further reduced.

Therefore, a robot surgery system for a single port surgery capable of securing a large workspace and a high degree of actuation freedom is required.

Figure 10:
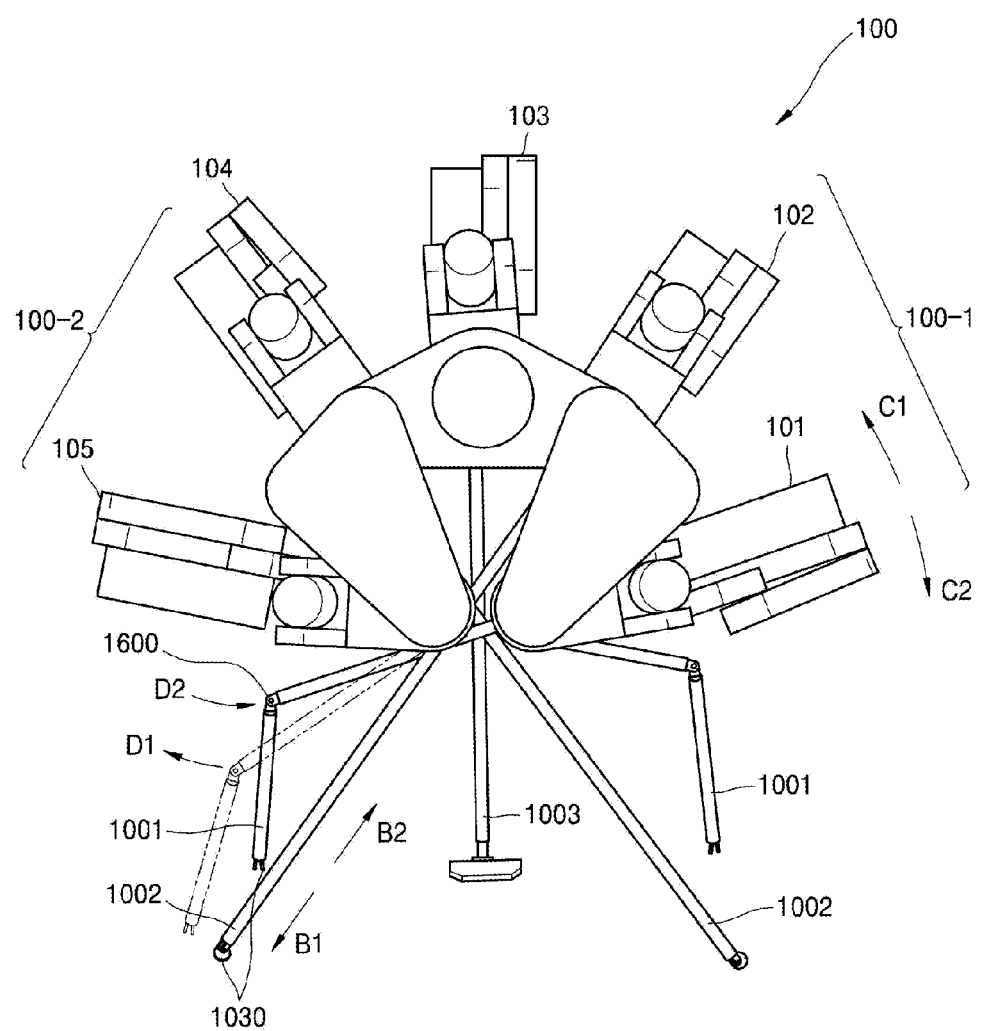
FIG. 10 is a perspective view of a robot arm unit employing a non-joint-type instrument and a joint-type instrument, according to one or more embodiments.

FIG. 10 is a perspective view of the robot arm unit 100 according to one or more embodiments. Referring to FIG. 10, according to one or more embodiments, the robot arm unit 100 may include the robot arm 101 (first robot arm) including the joint-type instrument 1001 and the robot arm 102 (second robot arm) including the non-joint-type instrument 1002. The robot arms 101 and 102 may be disposed to be adjacent to each other to form a first arm module 100-1. The joint- and non-joint-type instruments 1001 and 1002 may be inserted into a patient through the incision portion 30. In this regard, the elbow joint portion 1600 of the joint-type instrument 1001 may be bent so that the joint- and non-joint-type instruments 1001 and 1002 form a triangular structure having an affected part as an apex.

An operation of the joint- and non-joint-type instruments 1001 and 1002 approaching the affected part will now be described based on the above-described configuration.

In a case where the affected part is disposed far away from the incision portion 30, the surgical tools 1030 provided in the joint- and non-joint-type instruments 1001 and 1002, more particularly, end portions of the joint- and non-joint-type instruments 1001 and 1002, need to be moved in a direction of an arrow B1. To this end, the robot arm 102 may not need to pivot with respect to the RCM, and may move a multi-joint structure, i.e. the arms 111~115, to linearly move the non-joint-type instrument 1002 in the direction of the arrow B1. The robot arm 101 may pivot with respect to the RCM in a direction of an arrow C1. The elbow joint portion 1600 of the joint-type instrument 1001 may pivot and unfold in a direction of an arrow D1 as shown by a dotted line of FIG. 10. Then, the joint- and non-joint-type instruments 1001 and 1002 may form the triangular structure having the affected part away from the incision portion 30 as the apex.

In a case where the affected part is disposed closer from the incision portion 30, the robot arm 102 may move only the multi-joint structure to linearly move the non-joint-type instrument 1002 in a direction of an arrow B2. The robot arm 101 may pivot in a direction of an arrow C2. The elbow joint portion 1600 of the joint-type instrument 1001 may pivot and fold in a direction of an arrow D2 as shown in an unbroken line of FIG. 10. Then, the joint- and non-joint-type instruments 1001 and 1002 may form the triangular structure having the affected part closer from the incision portion 30 as the apex.

Locations of the robot arms 101 and 102 may be continuously changed during a surgery. According to one or ore embodiments, the robot arm 102 may be linearly reciprocated, and the robot arm 101 may be pivotally actuated, and thus the triangular structure of the joint- and non-joint-type instruments 1001 and 1002 may be maintained. That is, according to one or more embodiments, when the joint- and non-joint-type instruments 1001 and 1002 move in the same direction, the robot arms 101 and 102 may move in different directions. For example, when the joint- and non-joint-type instruments 1001 and 1002 move in the direction B1 or B2, the robot arm 102 may move linearly in the direction B1 or B2, and the robot arm 101 may pivot in the direction C1 or C2. As described above, a range for moving the robot arms 101 and 102 without being interfered may be increased, thereby possibly securing a large workspace, and a degree of work freedom of the joint- and non-joint-type instruments 1001 and 1002 may be improved, thereby possibly achieving a smooth and efficient surgery.

Figure 9D:
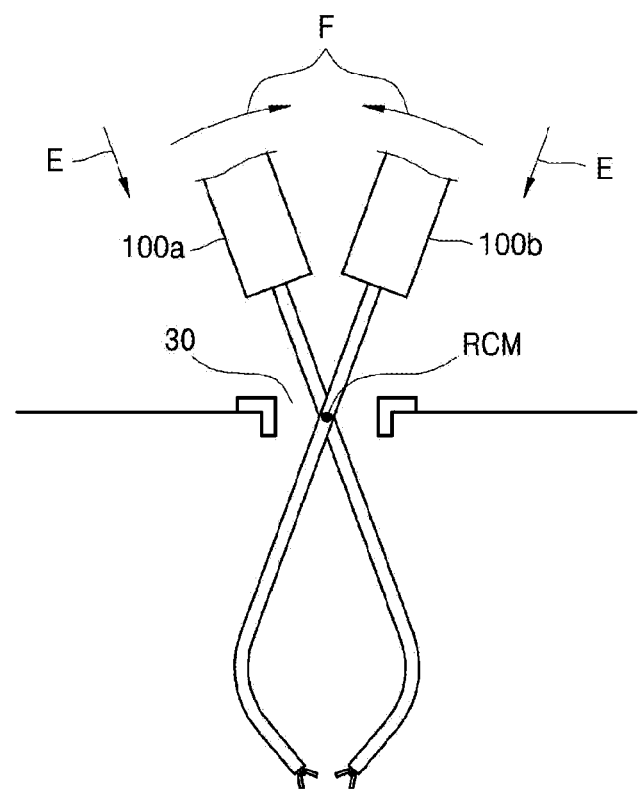
FIG. 9D illustrates a limited degree of work freedom in a single port surgery employing two bent instruments according to one or more embodiments.

As a comparison example, in a case where the two bent instruments 1004 of FIGS. 9C and 9D are employed, the robot arms 100a and 100b may need to rotate in a direction to which they approach each other so as to move the two instruments 1004 in the same direction (in a direction closer to or far from the incision portion 30), and thus, workspaces and a degree of work freed of the two instruments 1004 may be limited due to interference between the robot arms 100a and 100b.

The non-joint-type instrument 1002 is a linear-type instrument that does not include an elbow joint portion. Thus, the non-joint-type instrument 1002 may be useful for a surgical operation requiring a strong work force, compared to the joint-type instrument 1001, whereas the non-joint-type instrument 1002 may have a high degree of work freedom. Thus, a procedure requiring a strong work force may use the joint-type instrument 1001 and an elaborate procedure may use a joint-type instrument 1001 by pairing the joint-type instrument 1001 and the non-joint-type instrument 1002, thereby possibly achieving an effective surgical operation compared to a case of using the two bent instruments 1004 that do not have a degree of freedom of a joint shown in FIGS. 9C and 9D.

Referring to FIG. 10, the robot arm unit 100 may further include a second arm module 100-2. The second arm module 100-2 and the first arm module 100-1 may have a symmetrical structure. The non-joint-type instrument 1002 may be installed in the robot arm 104, and the joint-type instrument 1001 may be installed in the robot arm 105. As described above, the robot arms 102 and 104, in which the non-joint-type instrument 1002 that linearly moves may be installed, may be disposed to be adjacent to each other, thereby possibly reducing an interference possibility between the first and second arm modules 100-1 and 100-2, which may increase a degree of work freedom, and thus diverse surgical operations may be performed. The operation of the second arm module 100-2 and an effect arising therefrom are the same as those of the first arm module 100-1, and thus redundant descriptions thereof will be omitted here.

Referring to FIG. 10, the robot arm unit 100 may further include the robot arm 103 in which the endoscopic camera 1003 may be installed. In this case, the robot arm 103 may be disposed to be adjacent to the robot arms 102 and 104 in which the non-joint-type instrument 1002 may be installed. That is, the robot arm 103 may be disposed in the opposite direction of the robot arm 101 with respect to the robot arm 102. The robot arm 103 may linearly and pivotally move so as to move the endoscopic camera 1003 during the surgery. Therefore, the robot arm 103 may be disposed to be adjacent to the robot arms 102 and 104 that linearly move during the surgery, thereby possibly securing a large workspace of the robot arm 103.

As described above, in a surgical robot system including the robot arms 101~105, operating ranges of the robot arms 101~105 may be limited due to interference therebetween during a surgery. However, according to embodiment one or more embodiments, the first and second arm modules 100-1 and 100-2 may be formed by pairing the robot arms 101 and 105 in which the joint-type instrument 1001 is installed and the robot arms 102 and 104 in which the non-joint-type instrument 1002 is installed, and thus the robot arms 101 and 105 and the robot arms 102 and 104 may move in different directions during the surgery. Thus, a collision possibility between the robot arms 101 and 105 and the robot arms 102 and 104 may be reduced, and a surgical operation may be smoothly performed. Furthermore, the first and second arm modules 100-1 and 100-2 may be symmetrically disposed with respect to the robot arm 103 in which the endoscopic camera 1003 is installed, thereby possibly implementing an effective surgical robot system having a high degree of freedom.

Although RCMs of the robot arms 101~105 are not identified and are referred to as an RCM for convenience of description, one of ordinary skill in the art may understand that that locations of RCMS of the robot arms 101~105 are different so as to avoid interference therebetween.

It should be understood that the exemplary embodiments described therein should be considered in a descriptive sense only and not for purposes of limitation. Descriptions of features or aspects within each embodiment should typically be considered as available for other similar features or aspects in other embodiments. For example, one of ordinary skill in the art may understand that the surgical robot system and the method of operating the same according to the present inventive concept may be variously modified. Also, the support equipment and the surgical instrument according to the present inventive concept may be applied not only to surgical equipment or system but also to other equipment.

While aspects of the present invention have been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A surgical robot system for a single port surgery comprising:
   a first robot arm including a joint-type instrument having an elbow joint portion, the first robot arm providing a motion displacement to the joint-type instrument with respect to a remote center of motion (RCM); and
   a second robot arm including a non-joint-type instrument without the elbow joint portion, the second robot arm pairing with the first robot arm when the elbow joint portion is bent such that the joint-type instrument and the non-joint-type instrument form a triangular structure, the second robot arm providing a motion displacement to the non-joint-type instrument with respect to the RCM.

2. The surgical robot system of claim 1, further comprising:
   a third robot arm including an endoscopic camera, the third robot arm providing a motion displacement to the endoscopic camera with respect to the RCM, wherein
      the third robot arm is in an opposite direction of the first robot arm with respect to the second robot arm.

3. The surgical robot system of claim 1, wherein the first robot arm and the second robot form a first arm module, and the surgical robot system further comprises:
   a second arm module having a fourth robot arm and a fifth robot arm, the fourth robot arm including a joint-type instrument having an elbow joint portion and the fifth robot arm including a non-joint-type instrument without the elbow a joint portion, the second arm module being symmetrical with the first arm module.

4. The surgical robot system of claim 3, wherein the second robot arm of the first arm module and the fifth robot arm of the second arm module are adjacent to each other.

5. The surgical robot system of claim 3, further comprising:
   a third robot arm including an endoscopic camera, the third robot arm providing an RCM displacement to the endoscopic camera, wherein
      the third robot arm is between the first arm module and the second arm module.

6. The surgical robot system of claim 1, wherein the non-joint-type instrument is a linear-type instrument.

7. A surgical robot system for a single port surgery comprising:
   a first robot arm including a joint-type instrument having an elbow joint portion; and
   a second robot arm including a non-joint-type instrument without the elbow joint portion, the second robot arm pairing with the first robot arm when the elbow joint portion is bent such that the joint-type instrument and the non-joint-type instrument form a triangular structure.

8. The surgical robot system of claim 7, wherein the first robot arm and the second robot form a first arm module, and the surgical robot system further comprises:
   a second arm module having a third robot arm including a joint-type instrument having an elbow joint portion, and a fourth robot arm including a non-joint-type instrument without the elbow joint portion, the second arm module being symmetrical with the first arm module.

9. The surgical robot system of claim 8, wherein second robot arm of the first arm module and the fourth robot arm of the second arm module are adjacent to each other.

10. The surgical robot system of claim 7, wherein the first robot arm and the second robot arm provide a motion displacement with respect to an RCM to the joint-type instrument and the non-joint-type instrument, respectively.

11. The surgical robot system of claim 7, wherein the elbow joint portion comprises:
    a shaft pivotally connect to at least one of a first portion and a second portion of the first robot arm;
    an actuation rod connected to the first portion of the first robot arm; and
    a joint link connected to the actuation rod and to the second portion of the first robot arm, wherein
       when the actuation rod is pulled in a longitudinal direction with respect to the first portion of the first robot arm, the pulling force is transferred to the second portion of the first robot arm via the joint link.

12. The surgical robot system of claim 11, wherein the joint link is formed of an elastic material.

13. The surgical robot system of claim 11, wherein the joint link is formed of a rigid material.

14. A method of operating a surgical robot system for a single port surgery, the method comprising:
    preparing a first robot arm providing a motion displacement to a joint-type instrument having an elbow joint portion with respect to a remote center of motion (RCM) and a second robot arm providing a motion displacement to a non-joint-type instrument not having a joint with respect to the RCM;
    inserting the joint-type instrument and the non-joint-type instrument into a patient through a single port; and
    bending the elbow joint portion of the joint-type instrument and forming a triangular structure using the joint-type instrument and the non-joint-type instrument.

15. The method of claim 14, further comprising:
    linearly moving the non-joint-type instrument in a lengthwise direction.

16. The method of claim 15, further comprising:
    pivoting the joint-type instrument with respect to the RCM and actuating the elbow joint portion.

* * * * *